United States Patent
Green

(10) Patent No.: US 8,435,794 B2
(45) Date of Patent: May 7, 2013

(54) COLORIMETRIC TEST FOR ANTIMALARIAL ARTEMESIN DERIVATIVES

(75) Inventor: Michael D. Green, Winder, GA (US)

(73) Assignee: The United States of America, as Represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 12/741,434

(22) PCT Filed: Nov. 5, 2008

(86) PCT No.: PCT/US2008/082466
§ 371 (c)(1),
(2), (4) Date: Jul. 21, 2010

(87) PCT Pub. No.: WO2009/061808
PCT Pub. Date: May 14, 2009

(65) Prior Publication Data
US 2010/0297775 A1    Nov. 25, 2010

Related U.S. Application Data

(60) Provisional application No. 60/985,399, filed on Nov. 5, 2007.

(51) Int. Cl.
*G01N 33/00* (2006.01)
(52) U.S. Cl.
USPC .............. 436/93; 436/128; 436/164; 436/166
(58) Field of Classification Search .................... None
See application file for complete search history.

(56) References Cited

U.S. PATENT DOCUMENTS

| 3,718,605 A | 2/1973 | Lester et al. |
| 3,873,269 A | 3/1975 | Kraffczyk et al. |
| 4,892,833 A | 1/1990 | Weiss et al. |

FOREIGN PATENT DOCUMENTS

WO    03-048766    6/2003

OTHER PUBLICATIONS

Naik, H. et al Development and validation of high-performance liquid chromatography-mass specroscopy assay for determination of artesunate and dihydroartemisinin in human plasma, 2005, Journal of Chromatography B, vol. 816, pp. 233-242.*

(Continued)

*Primary Examiner* — Robert Xu
(74) *Attorney, Agent, or Firm* — Gifford, Krass, Sprinkle, Anderson & Citkowski, P.C.

(57) ABSTRACT

A process for testing a composition as containing an artemisinin derivative is provided that includes contacting the composition with a reagent made up of a hydrogen bonding polar organic solvent and an acid having a pK value of less than 3.8 at 25° Celsius and capable of acid catalyzing a decomposition reaction of the artemisinin derivative so as to provide a reaction mixture. The reaction mixture is allowed sufficient time at a reaction temperature for the artemisinin derivative to decompose to yield a colored decomposition product discerned by a normal unaided human eye. A kit for testing a composition for an artemisinin derivative according to the process is provided together with instructions for contacting the solvent and the acid with the composition to decompose the artemisinin derivative to yield the colored decomposition.

12 Claims, 2 Drawing Sheets

OTHER PUBLICATIONS

Guilin Pharmaceutical, Quality specification of artemisinin in the Pharmacopoeia 2005 edition, retrieved online from: http://www.guilinpharma.com/english/qinghaocenter/Empolder_list.asp?Action=34&id=221.*

* cited by examiner

COLORIMETRIC TEST FOR ANTIMALARIAL ARTEMESIN DERIVATIVES

CROSS-REFERENCE TO RELATED APPLICATIONS

This application is the U.S. national phase of PCT/US2008/082466 filed Nov. 5, 2008, which claims priority of U.S. Provisional Patent Application Ser. No. 60/985,399 filed Nov. 5, 2007, which is incorporated herein by reference.

STATEMENT REGARDING FEDERALLY SPONSORED RESEARCH OR DEVELOPMENT

The invention described herein may be manufactured, used, and licensed by or for the United States Government.

FIELD OF THE INVENTION

The present invention in general relates to a colorimetric assay for artemisinin derivatives, and in particular to an assay and a corresponding kit for testing an antimalarial dosage for artemisinin derivatives by producing an optically discernable green color.

BACKGROUND OF THE INVENTION

Malaria is a leading cause of mortality in children across the tropics. Additionally, the debilitating effects of malaria result in lost work productivity and consume considerable public healthcare resources in those regions. As a result, malaria is an element in a cycle of poverty and disease that can be effectively controlled through medicine, bed nets, and rudimentary mosquito control. Unfortunately, efforts to control malaria have been thwarted in many areas by the widespread proliferation of counterfeit and poor quality antimalarial drugs.

Poor quality drugs or counterfeits pose an immediate threat to public health and undermine malaria control efforts and contribute to observed treatment failures as well as expose malaria parasites to low drug levels, resulting in early loss of the usefulness of effective life-saving drugs, i.e. the artemisinins. There has been documented evidence of death as a result of patient unwittingly taking fake artesunate (Newton P N, McGready R, Fernandez F, Green M D, et al. (2006). Manslaughter by Fake Artesunate in Asia-Will Africa Be Next? PLoS Medicine 3: 1-4). The urgency of the problem was further highlighted by the report of an international multidisciplinary effort that recently led to a major bust of some of the counterfeit artesunate manufacturers (Newton P N, Fernandez F M, Plancon A, Mildenhall D C, Green M D, Ziyong Li, Christophel E M, Phanouvong S, Howells S, McIntosh E, Laurin P, Blum N, Hampton C Y, Faure K, Nyadong L, Soong C W R, Santoso B, Zhiguang W, Newton J, Palmer K (2008). A Collaborative Epidemiological Investigation into the Criminal Fake Artesunate Trade in South East Asia. PLoS Medicine 5 (e32):209-19.

A study detailed in the World Health Organization Fact Sheet 94 estimates that between 25 and 50 percent of medicines consumed in the developing world are counterfeit. A specific survey of antimalarial drugs conducted in Nigeria found 48 percent of all tested drugs were found to be of poor quality and 88 percent of the tested chloroquine phosphate tablets were of poor quality (Newton P N, McGready R, Fernandez F, Green M D, et al. (2006). Manslaughter by Fake Artesunate in Asia-Will Africa Be Next? PLoS Medicine 3: 1-4). A study reported in 2007 found that 29 percent of the tested artemisinin-derived antimalarials collected in Kenya and the Democratic Republic of Congo were under dosed and the samples with the lowest effective drug content were artemisinin injectables. Artemnkeng M A, DeCock K, Plaizier—Vercammen J (2007). Quality Control of Active Ingredients in Artemisinior—derived Antimalarials within Kenya and OR Congo. Tropical Medicine and International Health 1211-68-74.

The profiteering associated with the production of counterfeit and poor quality antimalarial drugs is expected to hamper World Health Organization efforts to use artemisinin combination therapy (ACT) in areas experiencing malaria. Owing to the high cost of artemisinin, the high demand created for the therapeutic created by World Health Organization promotion of this family of therapeutics, and poorly controlled drug chain of custody all create a favorable situation for the counterfeiting and producing of artemisinin compounds in dosages.

While the testing of artemisinin compounds in a dosage is a straightforward and routine process in a conventional analytical lab, field testing of antimalarials is often precluded by a lack of such facilities as a chromatograph, let alone a separation column coupled to a spectrometer such as infrared, mass, ultraviolet-visible, or nuclear magnetic resonance. Additionally, conventional analytical laboratory instrumentation is often functionally incompatible with the operating environment of a field health worker.

Green et al. have described colorimetric reactions of artemisinins, i.e. artesunate, dihydroartemisinin, and artemether using diazonium salts (Green M D, Mount D L, Wirtz R A (2001). Authentication of artemether, artesunate and dihydroartemisinin antimalarial tablets using a simple colorimetric method. Trop Med Int Health 6(12):980-2; Green M D, Mount D L, Wirtz R A, White N J. (2000). A colorimetric field method to assess the authenticity of drugs sold as the antimalarial artesunate. J Pharm Biomed Anal. 24(1):65-70). These reactions require the conversion of the artemisinin compound to unsaturated decalone or enolate/carboxylate followed by the reaction with the diazo dye to produce a yellow color. For artesunate and dihydroartemisinin, the conversion to the enolate/carboxylate was achieved by using a strong base, while artemether was converted to the decalone use a strong acid. The pH of the solutions were adjusted to 4 (artesunate and dihydroartemisinin) or 8 (artemether) in order for the reaction with the diazonium salt to occur. These methods required the use of a higher buffered solutions and a second derivatization step for the color to develop.

Thus, there exists a need for a safe, one step process for testing a composition for an antimalarial dosage present in a therapeutically effective amount of an artemisinin derivative that is inexpensive and colorimetric. Additionally, there exists for a kit embodying such a process that is operated by an individual with no laboratory training, equipment, or safety gear.

SUMMARY OF THE INVENTION

A process for testing a composition as containing an artemisinin derivative is provided that includes contacting the composition with a reagent made up of a hydrogen bonding polar organic solvent and an acid having a low pK value. and capable of acid catalyzing a decomposition reaction of the artemisinin derivative so as to provide a reaction mixture. The reaction mixture is allowed sufficient time at a particular reaction temperature for the artemisinin derivative to decompose to yield a colored decomposition product discerned by a normal unaided human eye.

A kit for testing a composition for an artemisinin derivative includes a quantity of the hydrogen bonding polar organic solvent as well as a quantity of an acid having a low pKa value able to react with the artemisinin derivative to catalyze decomposition. A reaction substrate is also provided together with instructions for contacting the solvent and the acid with the composition to decompose the artemisinin derivative to yield the colored decomposition product discernable by a normal unaided human eye.

DETAILED DESCRIPTION OF THE PREFERRED EMBODIMENTS

Figure 1:
FIG. 1 is a photograph depicting a selective color change for artemisinin derivatives scraped onto a white substrate and maintained at temperatures between 30 and 40° Celsius through contact with an exothermic chemical pack (these temperatures may also be achieved through contact with skin at normal human body temperature) after 10 minutes contact with a few drops of aqueous 5 weight percent acetic acid and 28 weight percent o-phosphoric acid.

The present invention has utility as a simple colorimetric test for a therapeutically effective amount of an artemisinin dosage within a composition. The present invention has further utility in allowing an individual with no formal laboratory training or equipment to test a composition with only nominal quantities of comparatively benign reagents.

As used herein an artemisinin derivative is defined as a molecule or salt containing a moiety of an endoperoxide. At present, commonly used antimalarial endoperoxides include artemisinin, artemether, dihydroartemisinin, arteether, and artesunate.

An inventive colorimetric test process involves dissolution of a quantity of composition to be tested for an artemisinin derivative in a hydrogen bonding polar organic solvent. The reaction of artemisinin derivatives with an acid in the presence of a hydrogen bonding solvent produces a distinctive color decomposition product based on the particulars of the test and thereby eliminate the necessity of buffered solutions as well as a second derivation step as was previously required in the aforementioned prior art colorimetric tests for artemisinin derivatives. The discovery of a colored product associated with acid catalyzed decomposition of the artemisinin derivative and colorimetric characterization of that derivative represents a novel attribute of the present invention. Additionally, as the present invention does not require toxic diazonium salts or highly flammable solvents of the prior art, the cost and safety of an inventive test is improved relative to the prior art. Additionally, through the acid-catalyzed decomposition of the artemisinin derivative now occurring in the presence of a weak acid, safety and cost of an inventive test are further reduced.

With the dissolution of an artemisinin derivative in a hydrogen bonding solvent, a concentration of greater than 1 milligram per milliliter of hydrogen bonding polar solvent, preferably in a concentration of between 2 and 20 milligrams per milliliter and subsequently adding thereto a volume of acid, a distinct color was noted after a temperature-dependent time period. Reaction at 20° Celsius typically occurred within 3 hours and is discernable in many instances after 30 minutes. It is appreciated that heating the reaction mixture to 40° Celsius typically shortens reaction times complete reaction to under an hour and typically is discernable in 2 to 15 minutes.

A hydrogen bonding polar organic solvent operative in the present invention has a degree of interaction with an artemisinin derivative during acid catalyzed decomposition so as to yield a color decomposition product. Preferably, the color decomposition product generated in hydrogen bonding polar organic solvent according to the present invention is green although it is appreciated that the rose colored decomposition product produced in acetone is also operative herein. Less polar solvents than those used in the present invention are observed to inhibit or indeed even retard formation of the colored artemisinin decomposition product. Notable among the inoperative solvents are dimethyl sulfoxide and isopropanol. Specific examples of operative solvents herein illustratively include methyl cellusolve, methanol, ethanol, acetone, acetonitrile, acetic acid, fluoro analogs thereof, perfluoro analogs thereof, and combinations thereof. In addition to experimental testing to determine feasibility of a given solvent as being acceptable as a hydrogen bonding polar solvent according to the present invention, resort to the unified solvation model allows one to predict feasibility of a given solvent within an inventive test. (S Joerg, R S Drago, and J Adams, (1997) Donor-acceptor and polarity parameters for hydrogen bonding solvents. J. Chem. Soc. Perkin Trans. 2:2431-2438). And in particular treatment of polar solvents as donors toward strong acid solutes as fit according to Equation 3). In particular, acetic acid is noted to be benign and to form cyclic dimers in solution with the dimer ring structure being broken upon the carboxyl proton undergoing an interaction with the artemisinin derivative or acid component of a reagent.

The nature of the acid suitable to catalyze an artemisinin derivative decomposition to produce a colored decomposition product is only limited by compatibility with the hydrogen bonding polar solvent and a pK (at 25° Celsius) sufficient to protonate a specific artemisinin derivative. An acid of a pK value less than 3.8 and preferably less than 3.4 are operative herein. It is appreciated that a high pK value acid can be made more effective by reaction mixture heating. Acids operative in the present invention illustratively include acids having a single proton capable of dissociation and multiple protons capable of dissociation so long as the first step dissociation has a pK value of less than 3.8 and capable of artemisinin derivative reaction. These acids illustratively include: aceto acetic o-amino benzo sulfonic, benzo sulfonic, bromo acetic, o-bromo benzoic, chloro acetic, chloro benzoic, chloro phenoxy acetic, citric, cyano acetic, cyano butric, cyano phenoxy acetic, dichloro acetic, dihydroxy malic, dimethyl malic, fluoro benzoic, o-hydroxy benzoic, malic, malonic, naphthalene sulfonic, o-nitro benzoic, oxalic, picric, tartaric; and inorganic acids of: hydrofluoric, o-phosphoric, phosphorus, pyrophosphoric, sulfuric, sulfurus, nitric, and hydrochloric.

Preferably, the acid is chosen that is a weak acid to lessen the possibility of a chemical burn associated with individual using an inventive test and not complying with acceptable safety procedures.

To facilitate field testing of tablets for an effective amount of artemisinin derivative, an inventive kit is provided inclusive of a strip of solid white substrate against which the colored decomposition product is discernable. By abrading a dosage tablet or shaking powder from a capsule believed to contain a therapeutically effective amount of an antimalarial artemisinin derivative until fine powder residue is noted on the paper, with the addition of a few drops of solvent reagent mixture containing portions of acid catalyst and hydrogen bonding polar organic solvent, a distinctive color develops indicative of the presence of therapeutically meaningful amounts of an artemisinin derivative. It is appreciated that more detailed results are obtained through resort to an artemisinin derivative control tablet or other dosage such as a capsule form containing a known quantity of a given artemisinin derivative. Additionally, it is appreciated that the deposition of different amounts of tablet material on a test strip, either produced through serial dilution or a varying number of abrasive passes that an approximate concentration study as to artemisinin derivative quantity in a tablet is so obtained. A concentration proportional color intensity of the decomposition product is observed. As noted in FIG. 1, the quantity of material abraded from a tablet dosage is sufficiently small that somewhere approximately between 1 and 10 percent of the tablet mass that tablet dosage after testing remains a therapeutically effective dosage for an individual.

It is appreciated that a file or other abrasive surface is optionally used to create a powder from a compacted tablet or other form of dosage such as a capsule believed to contain an artemisinin derivative and the powder then deposited on a conventional pale colored or white substrate for subsequent reagent addition to determine if the artemisinin derivative is present. It is further appreciated that testing of a powdered artemisinin derivative can be done by simply depositing a few milligrams of the test powder onto a substrate for subsequent addition of reagents or alternatively for dissolution in a vial containing the reagents. Optionally, an abrasive grit is adhered onto the solid substrate to more efficiently utilize tablet powder.

The present invention is further detailed with respect to the following examples that are not intended to limit the scope of the appended claims.

EXAMPLE 1

Methanol is added to the following drugs to yield mixtures or solutions at concentrations of 10 milligrams/milliliter (mg/ml): artemether (AM), sulfadoxine (SDX), lumefantrine (LF), artesunate (ARTS), dihydroartesunate (DQHS), chloroquine phosphate (CQ), quinine sulfate (Q), arteether (AE), pyrimethamine (pyr), aspirin (ASA), chloramphenicol (CA), acetaminophen (Aceta), artemisinin (QHS), amoxicillin (Amox), ciprofloxacin (Cipro), erythromycin (Ery), tetracycline (Tet) and a blank (B). Samples are visually assessed for color after reacting for 2 hours at 20° C. Insoluble mixtures are allowed to settle and 0.5 ml was transferred to a glass tube. 0.5 ml of aqueous 85% by weight o-phosphoric acid is added to each sample. The samples were allowed to react at room temperature for 2 hours. Absorbance spectra are taken from the artemether sample. Two distinct absorbance peaks were apparent at 449 and 523 nm. The results are provided in Table 1.

TABLE 1

Colorimetric results for drugs in methanol (10 mg/ml) with 0.5 ml 85 wt % o-phosphoric acid after 2 hours at 20° C.

| Drug | Color |
|---|---|
| artemether | green |
| sulfadoxine | colorless |

TABLE 1-continued

Colorimetric results for drugs in methanol (10 mg/ml) with 0.5 ml 85 wt % o-phosphoric acid after 2 hours at 20° C.

| Drug | Color |
|---|---|
| lumefantrine | colorless |
| artesunate | green |
| dihydroartesunate | Yellow/green |
| chloroquine phosphate | colorless |
| quinine sulfate | colorless |
| arteether | green |
| pyrimethamine | colorless |
| aspirin | colorless |
| chloramphenicol | colorless |
| acetaminophen | colorless |
| artemisinin | green |
| amoxicillin | colorless |
| ciprofloxacin | colorless |
| erythromycin | colorless |
| tetracycline | colorless |
| blank control | colorless |

EXAMPLE 2

Artemether is prepared in methanol at the following concentrations: 0, 1, 5, 10, 20 mg/ml. 0.1 ml is added per well of a polystyrene 48-well plate. 0.1 ml of 85 wt % aqueous o-phosphoric acid is added and the mixture allowed to react at room temperature for 3 hours. Color intensity is assessed from a digital photograph of the plate using pixel analysis software. Using the Red vs. Blue option of the software, values for each well were recorded. The concentration vs. % Red vs. Blue reveals a linearity coefficient ($R^2$) of 0.98 indicating that color intensity correlated well with concentration revealing a quantitative test.

EXAMPLE 3

The procedure of Example 2 is repeated with the replacement of 85 wt % o-phosphoric acid in separate experimental series with (A) 5 wt % HCl, (B) 5 wt % oxalic acid, and (C) 5 wt % sulfuric acid. Comparable linearity to Example 2 as a function of concentration is provided for each of series (A)-(C).

EXAMPLE 4

Artemether is prepared at a concentration of 10 mg/ml in each of the following solvents: DMSO, isopropanol, methyl cellosolve, methanol, acetone, and acetonitrile. 85 wt % aqueous o-phosphoric acid is added at a ratio of 1:1. Absorbance and color were assessed at various time points and shown in Table 2.

TABLE 2

Artemether acid-catalyzed colorimetric decomposition as a function of solvent and time.

| Solvent | 5 min | 30 min | 60 min | 180 min |
|---|---|---|---|---|
| DMSO | yellow | yellow | yellow | yellow |
| Isopropanol | colorless | colorless | colorless | colorless |
| Methyl cellosolve | yellow | green | green* | green* |
| Methanol | rose | green | green | green |
| Acetone | rose | rose | rose | rose |
| Acetonitrile | yellow | green | green* | amber |
| % Acetic acid (aqueous) | rose | green* | green* | green* |

*denotes high intensity color

At 4 hours incubation, the intensity/absorbance continued to increase. Heating the samples to between 30 and 40° C. and solvent reflux significantly increased color intensity thereby reducing the amount of time required to observe the terminal color reaction (~30 min). The property of a hydrogen bonding solvent in having a $E_B$ of between less than 2 is in agreement with these results. These results are reproduced with (A) 5 wt % HCl, (B) 5 wt % oxalic acid, and (C) 5 wt % sulfuric acid.

EXAMPLE 5

To minimize the potential of material resistance developing against artemisinin compounds, combination therapy requires the use of an artemisinin drug (e.g., artemether or artesunate) combined with an antimalarial possessing a relatively long half-life (e.g., lumefantrine or amodiaquine). One such drug currently being used in Africa is COARTEM (Artemether+Lumefantrine). It was observed that Lumefantrine formed a distinct reddish colored ion-paired complex with Congo Red under acidic conditions.

Colorimetric Assays that Assess Lumefantrine as Well as Artemether in a Combination Drug Tablet Method for Lumefantrine determination: Add 0.5 ml of methanol to the wells of a 24-well polystyrene plate. Add 10-40 microliters of Lumefantrine (10 mg/ml in ethyl acetate). Add 1 ml of 1.1 M acetic acid and 0.1 ml of congo red (1 mg/ml in water). A reddish color immediately develops with a homogeneous distribution of a red precipitant. The color intensity of a digital photograph was assessed using color pixel software. Linearity coefficient ($R^2$) of the concentration vs. pixel plot was 0.99 for 0-40 microliters and the test would be considered quantitative.

Method for Artemether and Lumefantrine Determination in a Coartem Tablet

Weigh and split a Coartem tablet (20 mg artemether, 120 mg lumefantrine). Weigh each split portion. Pulverize each portion. To one portion, add enough methanol to achieve an artemether concentration of 10 mg/ml. To the other portion add ethyl acetate to achieve a lumefantrine concentration of 10 mg/ml. Prepare reference standards of artemether and lumefantrine. For the Artemether test, add 0.2 ml of artemether reference standard or sample to each well of a 24-well plate. Then add 0.2 ml of 85% o-phosphoric acid and wait ~4-5 hours. For the lumefantrine test, combine 50 microliters of reference or sample with 0.5 ml of methanol, 1 ml of 1:1 M acetic acid and 0.1 ml of congo red (1 mg/ml water). Samples and reference standards were prepared in triplicate. Color pixel analysis was used to measure color intensity.

The reference standard concentrations are formulated to represent % active pharmaceutical ingredient (% API). 100% indicates that the amount detected is exactly what is stated by the manufacturer. For colorimetric assays, sample APIs between 80% and 120% are considered acceptable. Values for the triplicates are averaged and graphed. The artemether and lumefantrine concentration of this particular Coartem tablet were well within the 80% to 120% range and would be considered acceptable. There is no interference from the yellow color of lumefantrine in the test of Example 1 for Artemether because lumefantrine has very low solubility in methanol.

EXAMPLE 6

As a confirmatory test, a pH indicator based test is provided for artesunate. The pH of artesunate is ×3.5 while fakes and common aminoquinoline antimalarials are more basic. An indicator dye has been discovered, bromochlorophenol blue salt (BCPB), which transitions from yellow to blue from pHs 3 to 4.5 (pH ~3.5-4.0 the dye is green). Therefore, presence of relatively pure artesunate will result in a green color.

A few mg of each of the following drugs are added to 0.5 ml of water and vortexed: artemether (AM), sulfadoxine (SDX), lumefantrine (LF), artesunate (ARTS), dihydroartesunate (DQHS), chloroquine phosphate (CQ), quinine sulfate (Q), arteether (AE), pyrimethamine (pyr), aspirin (ASA), chloramphenicol (CA), acetaminophen (Aceta), artemisinin (QHS), amoxicillin (Amox), ciprofloxacin (Cipro), erythromycin (Ery), tetracycline (Tet) and a blank (B). About 4 drops of BCPB (1 mg/ml in water) is added to each sample. Color changes are immediately observed with only artesunate changing the color of blue BCPB to green. Aspirin turned BCPB yellow due to its acidity; the other drugs turned BCPB various shades of blue or purple.

EXAMPLE 7

The test of Example 6 is repeated on a solid substrate. All drugs described in Example 6 are prepared in acetone at 10 mg/ml (except for Cipro at 1 mg/ml). A drop is added to filter paper (Whatman 17Chr) and allowed to dry. A few drops of BCPB solution is added to each sample and again the presence of artesunate resulted in a green color while aspirin, being acidic, turned BCPB yellow. The rest of the drugs turned BCPB to various shades of blue and purple.

EXAMPLE 8

About 1-10 mass % of a tablet is rubbed onto a rough, pale colored or preferably white surface of an emery board, resulting in a residue of fine powder. A strip with dimensions of a few mm across (e.g. 2-5 mm) and several mm long (e.g. 5-10 mm) is adequate to sample enough tablet material for the test.

The strips are placed on a commercially available exothermic hand warmer heating pack. The pack is a conventional bag containing charcoal, salt, water, iron powder, and vermiculite and is exposed to air to produce an exothermic reaction lasting for several hours. The temperature of the reaction is approximately 34-37° C. The heat from this device greatly enhances the reaction time of the test from a few hours at room temperature to about 5-10 minutes.

A few drops of premixed reagents of solvent and acid per Example 4 are added to the material on the strip. A green color develops when artesunate, artemether, arteether, or dihydroartemisinin (DHA) is present in the tablet without interference from other tablet co-drugs or adjuvants. Drugs such as aspirin, chloroquine, acetaminophen, and sulfadoxine/pyrimethamine (S/P) remain colorless as shown in FIG. 1. The dihydroartemisinin was present in Cotecxin. The assay has also been tested with amoxicillin, erythromycin, ciprofloxacin, ampicillin, lumefantrine, tetracycline, chloramphenicol, and quinine. Erythromycin exhibited a yellow color while the rest (except for tetracycline which is initially yellow) remained colorless. These tests were conducted by adding the reagent to a few milligrams of each drug and allowing the reaction to proceed at room temperature for about 1.5 hours. The reaction time may be significantly shortened to 5-10 minutes by heating as described in the current test methodology (see above). Although a color is apparent after a few hours at room temperature, it was observed that slight heating of the reaction mixture with the exothermic packet or contact with skin at normal human body temperature enhanced color intensity as well as decrease the time needed for the color to develop. Without intending to be bound to a particular theory it is believed that the heating results in a better yield of the colored decomposition product by minimizing formation of other decomposition products.

EXAMPLE 9

Figure 2:
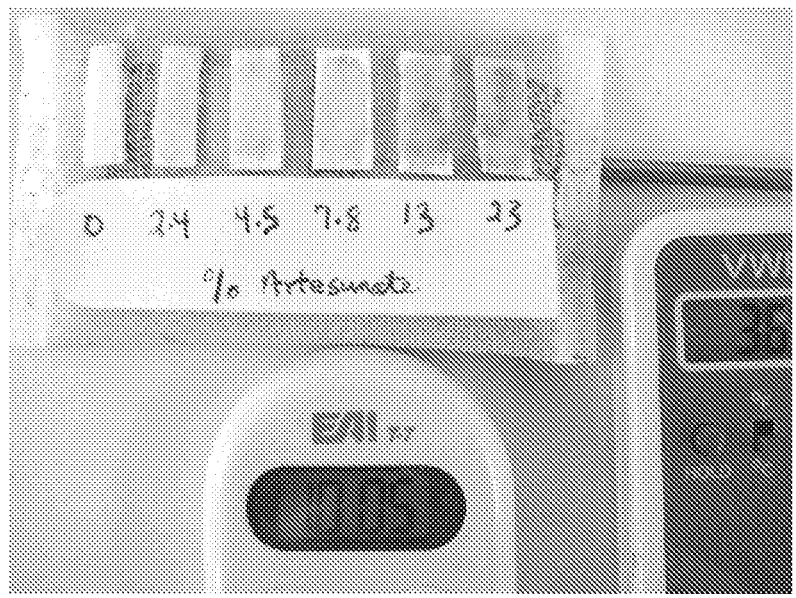
FIG. 2 is a photograph showing concentration dependent coloration for artesunate on a white substrate after contact with a reagent solution of 5 weight percent water, 28 weight percent o-phosphoric acid and methanol.
Figure 3:
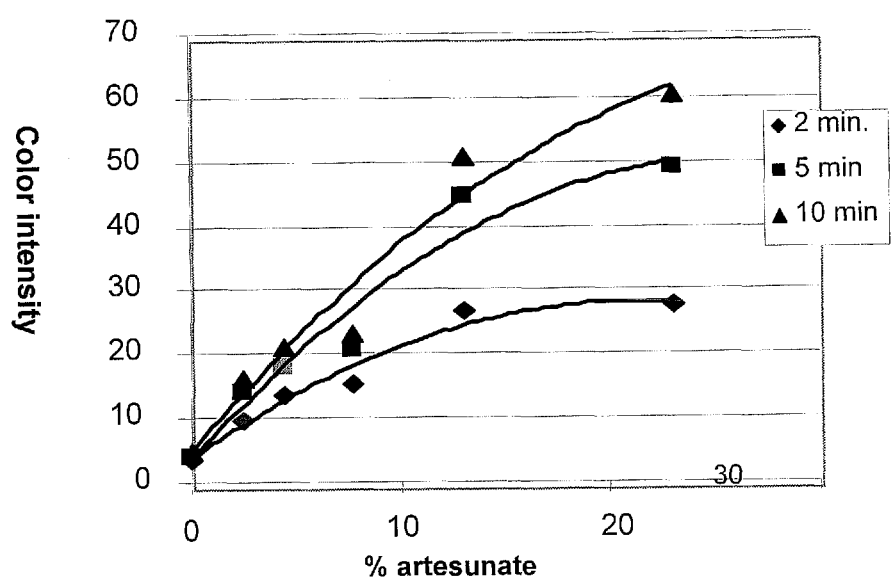
FIG. 3 is a plot of color intensity as a function of percent artesunate per the inventive test color after 2 minutes (diamond), 5 minutes (square) and 10 minutes (triangle) derived from FIG. 2.

Various proportions of artesunate are thoroughly mixed with tablet excipients (typical mixture of inactive ingredients) to yield mixtures containing 0, 2.4, 4.5, 7.8, 13, and 23% artesunate. A typical artesunate tablet contains about 17% artesunate. About 2 milligrams of the powder are distributed across small strips of emery board material to simulate the scraping of a typical tablet. The strips are placed on the "hand warmer" and one drop of reagent added. Photos were taken at 2, 5, and 10 minutes while the mixture is incubating on the hand warmer (T=36° C.). A yellowish-green color is observed as low as 2.4% artesunate. The 10 minute photograph shows a concentration dependent coloration, FIG. 2. The intensity of the green color was assessed using image analysis software (FIG. 3). The software (HVImagePCv8, Global Systems Science, U. of California; http://mvh.sr.unh.edu/software/software.htm) measures the average frequency of pixels of a particular color in a given area. Results indicate that a reaction time of 5 to 10 minutes on the hand warmer is sufficient to produce a visually distinct color. There is little visual difference in color intensity between 13 and 23% artesunate indicating the assay is approaching saturation. A counterfeit drug with 8% artesunate (about ½ of a genuine tablet) or less is easily distinguished.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for testing a composition for the presence of an artemisinin derivatives comprising:

contacting the composition with a reagent, said reagent consisting of a hydrogen bonding polar organic solvent and an acid having a pK value of less than 3.8 at 25° Celsius and catalyzing acid decomposition of the artemisinin derivative; and allowing sufficient time at a reaction temperature for the artemisinin derivative to decompose to yield a colored decomposition product discernable by a normal unaided human eye.

2. The process of claim 1 wherein said colored decomposition product is green.

3. The process of claim 2 wherein said colored decomposition product has a visual intensity that is proportional to concentration.

4. The process of claim 1 wherein the composition comprises the artemisinin derivative and at least one component of tablet adjuvants, antimicrobials, non-artemisinin derivative antimalarials and nonsteroidal anti-inflammatories.

5. The process wherein said hydrogen bonding polar organic solvent is methanol, ethanol, methylcellusolve, acetonitrile, acetic acid, acetone, or a combination thereof.

6. The process of claim 1 wherein said hydrogen bonding polar organic solvent is methanol.

7. The process of claim 1 wherein said hydrogen bonding organic solvent is acetic acid or phosphoric acid.

8. The process of claim 1 wherein the reaction temperature of the reaction mixture is between 30 and 40° Celsius and a boiling temperature of said hydrogen bonding polar organic solvent.

9. The process of claim 8 wherein the reaction temperature is between 30 and 40° Celsius and the reaction time is from 2 to 15 minutes.

10. The process of claim 1 further comprising abrading the composition from an oral dosage.

11. The process of claim 1 wherein contact between the composition and said reagent is through dissolution of the composition in said reagent.

12. The process of claim 1 wherein the composition comprises artesunate and further comprising contacting a second portion of the composition with water and a pH indicator showing a color change at pH between 3.5 and 4.0.

* * * * *